United States Patent
Selim et al.

(10) Patent No.: US 7,260,440 B2
(45) Date of Patent: *Aug. 21, 2007

(54) METHOD AND APPARATUS FOR MEASUREMENT OF PRESSURE AT A DEVICE/BODY INTERFACE

(75) Inventors: Andrew Selim, Caringbah (AU); Patrick John McAuliffe, Chatswood (AU); Milind Chandrakant Raje, Wentworthville (AU); Robert Henry Frater, Lindfield (AU)

(73) Assignee: ResMed Limited, Bella Vista (AU)

( * ) Notice: Subject to any disclaimer, the term of this patent is extended or adjusted under 35 U.S.C. 154(b) by 0 days.

This patent is subject to a terminal disclaimer.

(21) Appl. No.: 11/191,952

(22) Filed: Jul. 29, 2005

(65) Prior Publication Data

US 2005/0261792 A1    Nov. 24, 2005

Related U.S. Application Data (63) Continuation of application No. 10/720,175, filed on Nov. 25, 2003, now Pat. No. 6,941,182.

(60) Provisional application No. 60/429,066, filed on Nov. 26, 2002.

(51) Int. Cl.
  *G06F 19/00*  (2006.01)
  *A61B 19/00*  (2006.01)

(52) U.S. Cl. ............... 700/97; 600/587; 73/37

(58) Field of Classification Search .......... 700/97, 700/117; 703/11; 73/37, 40, 46, 49.8, 862.53, 73/862.581, 862.582; 702/138, 139; 600/587; 128/206.4
See application file for complete search history.

(56) References Cited

U.S. PATENT DOCUMENTS 3,690,148 A * 9/1972 Snowdon et al. ............ 73/37

| | | | |
|---|---|---|---|
| 3,760,637 A | 9/1973 | Budinger et al. | |
| 4,503,705 A | 3/1985 | Polchaninoff | |
| 4,873,994 A | 10/1989 | Anger et al. | |
| 5,734,095 A | 3/1998 | Lamerdin et al. | |
| 6,315,739 B1 | 11/2001 | Merilainen et al. | |
| 6,728,589 B1 | 4/2004 | Delache et al. | |
| 6,941,182 B2 * | 9/2005 | Selim et al. ............ | 700/97 |
| 2004/0117165 A1 | 6/2004 | Selim et al. | |

FOREIGN PATENT DOCUMENTS

WO    WO 01/43804    *    6/2001

* cited by examiner

*Primary Examiner*—Leo Picard
*Assistant Examiner*—Steven R. Garland
(74) *Attorney, Agent, or Firm*—Nixon & Vanderhye P.C.

(57) ABSTRACT

A system and method for measuring contact pressures between two surfaces, and especially, between the body and a device resting on the body, e.g., the skin and a breathable gas mask. A deformable, resilient probe having a flow passage therein is initially placed between the two surfaces such that the flow passage is blocked. Fluid pressure within the probe is then increased until the pressure in the probe overcomes the contact pressure between the two surfaces, such that fluid begins to flow through the flow passage in the probe. The pressure at which the fluid begins to flow through the flow passage in the probe is recorded as the contact pressure between the two surfaces. Contact pressure maps created using this apparatus and method may be used to create anthropometric models of the face and other body parts.

3 Claims, 8 Drawing Sheets

METHOD AND APPARATUS FOR MEASUREMENT OF PRESSURE AT A DEVICE/BODY INTERFACE

CROSS REFERENCE TO RELATED APPLICATION

This is a continuation application of U.S. application Ser. No. 10/720,175, filed Nov. 25, 2003, now U.S. Pat. No. 6,941,182, which claims the benefit of U.S. Provisional Application Ser. No. 60/429,066, filed Nov. 26, 2002, each incorporated herein by reference in its entirety.

BACKGROUND OF THE INVENTION

1. Field of the Invention

The present invention relates generally to devices for measuring contact pressures between two interfacing components, and more particularly, to measuring pressures between skin and a component placed thereon.

2. Description of Related Art

Many medical devices, clothing items, and other objects are designed to rest against the body during operation. For many of these devices, a proper fit of the device against the body is desirable for user comfort and/or proper device function.

For example, breathable gas delivery masks are used in many types of medical treatments, ranging from simple oxygen therapy to the treatment of obstructive sleep apnea by application of continuous or variable positive airway pressure. These masks are usually designed to rest against the skin adjacent the nose, or in some cases, the nose and mouth. The portion of the mask that rests against the skin is usually a soft, conforming cushion or flange. A good seal between the mask and the skin facilitates delivery of breathable gas. Gas leaks between the mask and the skin reduce the volume of gas delivered to the patient, thus reducing the efficacy of the treatment.

Anthropometric data on the human face (i.e., normalized measurements of facial dimensions) can be used to design breathable gas masks so that they make better seals with the skin. However, anthropometric data on the human face does not describe the response of the facial tissues to the mask, and thus, there are certain circumstances in which pure anthropometric data may be insufficient. One such circumstance occurs when positive airway pressure systems are used. These systems deliver breathable gas at substantial pressures in order to pneumatically splint a patient's airway. If a breathable gas mask is used with a positive airway pressure system, the pressures created by the system may cause the facial tissues to deflect, and at higher pressures, may cause the mask to lift away from the face. In these circumstances, the complex response of the facial tissues to the applied pressures makes it more difficult to design a well-fitting mask.

Data on the operational contact pressures between a breathable gas mask and the skin on which it rests can be used in lieu of or in addition to available anthropometric data in order to design masks with better fit. However, data on the contact pressures between a breathable gas mask and skin while the mask is in use is more difficult to obtain than anthropometric data.

Similar problems in obtaining good anthropometric data and predicting the skin's response to applied pressures occur when attempting to design and fit other objects, such as shoes, harnesses, orthotics, prosthetics, headgear for securing breathable gas masks, backpacks, and/or items of clothing, particularly with elastic properties and/or elements.

SUMMARY OF THE INVENTION

One aspect of the invention relates to an apparatus for measuring contact pressures between two surfaces and, particularly, between a breathable gas mask and the face.

Another aspect of the invention relates to a method of measuring a contact pressure/force between two surfaces, e.g., curved and/or deformable surfaces, and, particularly, between a breathable gas mask and the face.

A further aspect of the invention relates to a method of dynamically measuring and monitoring contact pressure between a cushion of a breathable gas mask and a portion of the face.

Yet another aspect of the invention relates to a method of designing a breathable gas mask using the measurement methods described above.

Another further aspect of the invention relates to a method for creating an anthropometric model of a face.

In particular, one embodiment of the apparatus for measuring contact pressures between two surfaces comprises a deformable, resilient probe having a flow passage therein. The probe is adapted to be inserted between the two surfaces such that the flow passage is substantially blocked in a first operative position of the probe. The apparatus also includes a fluid flow generator coupled to the probe, a fluid flow meter coupled between the fluid flow generator and the probe, and a manometer coupled between the fluid flow generator and the probe. The apparatus may also include a data acquisition system coupled to at least the fluid flow generator and the manometer.

Additionally, the method for measuring a contact pressure between two surfaces generally comprises inserting at least one deformable, resilient probe having a flow passage therein between the two deformable surfaces such that the flow passage is substantially blocked in a first operative position. The method also comprises generating fluid pressure within the probe, measuring the fluid pressure within the probe, measuring fluid flow through the probe, and recording the fluid pressure at which the fluid flow increases above a baseline flow value as the contact pressure.

These and other aspects, features, and advantages of the invention will be described below.

BRIEF DESCRIPTION OF THE DRAWINGS

The present invention will be described with respect to the following Drawings, in which like numerals represent like features throughout the several views, and in which.

DETAILED DESCRIPTION

Figure 1:
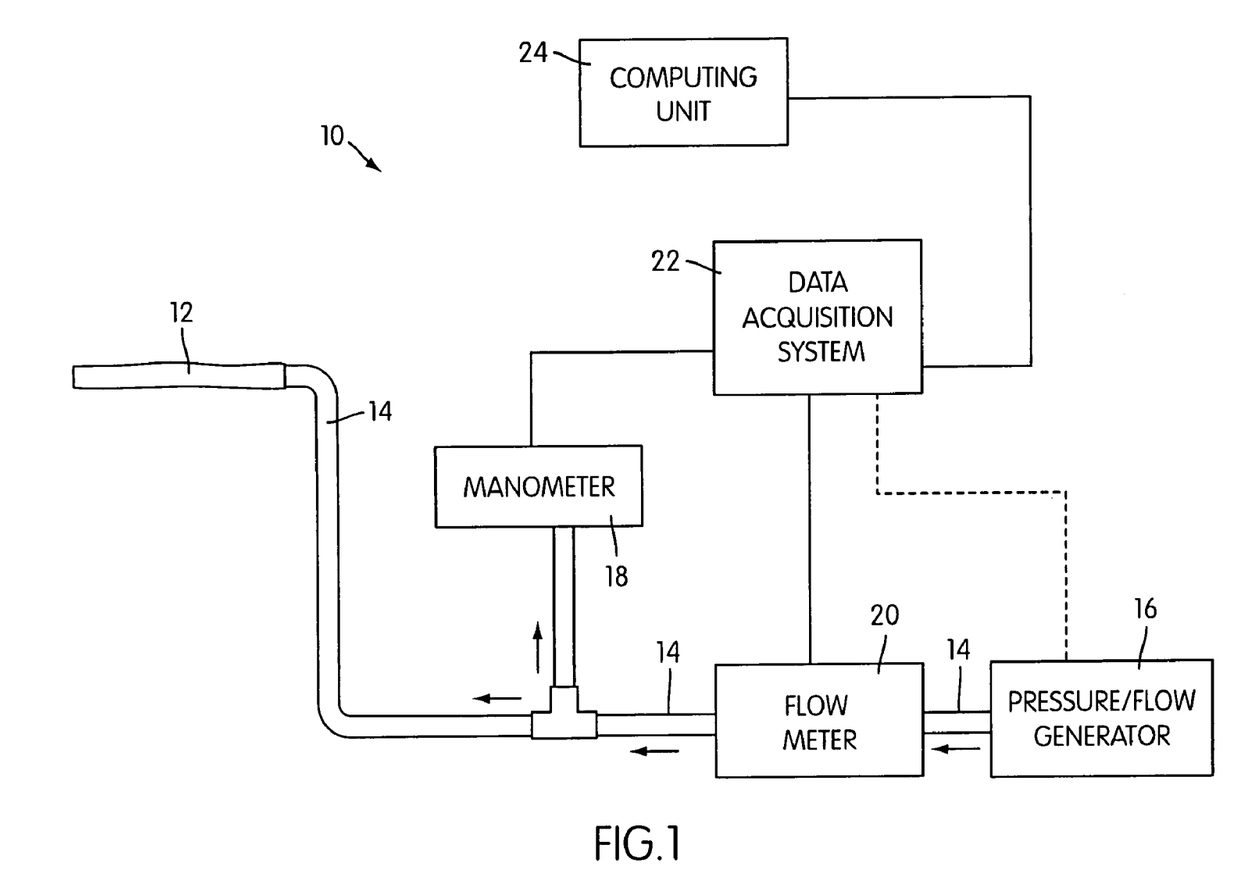
FIG. 1 is a schematic diagram of a pressure measurement system according to an embodiment of the present invention.

A pressure measurement system 10 according to an embodiment of the present invention is illustrated in the schematic view of FIG. 1. In general, the pressure measurement system 10 is configured and adapted to measure contact pressures between two surfaces. More particularly, the pressure measurement system 10 is well suited for measuring contact pressures between two curved and/or deformable surfaces. This is not possible with conventional microstrain gauges due to hysterisis calibration issues. Certain aspects of the pressure measurement system 10 and methods for using it will be described below with respect to measuring contact pressures between skin and a breathable gas mask, although the pressure measurement system 10 may be used to determine contact pressures between the body and other objects, such as shoes, harnesses, orthotics, prosthetics, headgear for securing breathable gas masks, and backpacks.

The pressure measurement system 10 comprises a deformable pressure measurement vessel or probe 12 which is connected by a length of tubing 14 to a flow generator 16. The flow generator 16 may include a control valve. Connected in series with the probe 12 and the flow generator 16 is a flow meter 20. A manometer 18 is connected to the tubing 14 at a position downstream from the flow meter 16 to measure the pressure within the tubing 14. The manometer 18 and flow meter 20 of this embodiment are digital instruments and are connected to a data acquisition system 22. (The dotted-line connection between the flow generator 16 and the data acquisition system 22 in FIG. 1 indicates that the flow generator may optionally be connected to or in communication with the data acquisition system 22.) The data acquisition system 22 is, in turn, connected to a computing unit 24, which may perform further analysis on the collected data. Each of these components will be described in more detail below.

Figure 2:
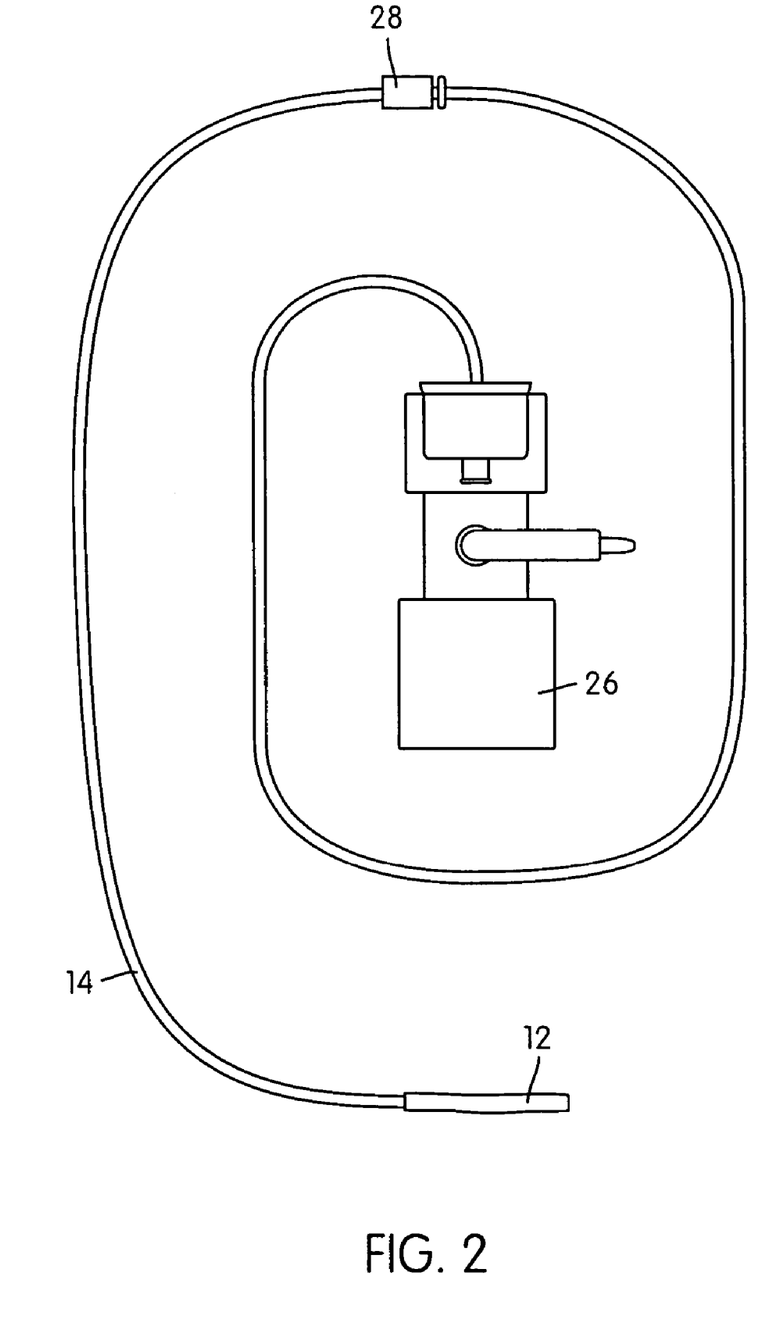
FIG. 2 is a top plan view of the pressure measurement probe.
Figure 3:
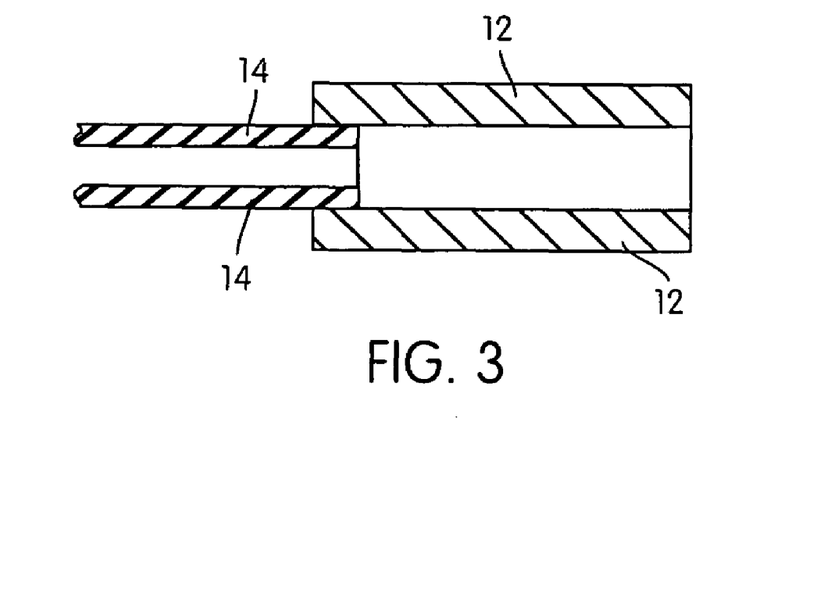
FIG. 3 is a cross-sectional view of the pressure measurement probe.

The probe 12 and a section of tubing 14 are shown in more detail the top plan view of FIG. 2. The probe 12 is a thin flexible, resilient tubular membrane that is connected to the tubing 14 on one end and is open to the atmosphere on the other end. The probe 12 may be connected to the tubing 14 by adhesives or other conventional type of connection. In general, any connection that produces an airtight seal between the probe 12 and tubing 14 is suitable. The probe 12 of this embodiment is formed of silicone rubber by a known process, such as dip molding. The probe 12 may also be made of a metal foil or composite material. FIG. 3 is a cross-sectional view of the probe 12 illustrating tubular nature of the probe 12 and the connection between the tubing 14 and probe 12.

The tubing 14 may be any sort of flexible tubing that is compatible with the fluids that are to be used. For example, in breathable gas mask contact pressure measurement applications, silicone rubber or flexible PVC tubing is suitable. In general, those of ordinary skill in the art would be capable of selecting flexible tubing with appropriate inner and outer diameters, pressure ratings, and other characteristics. For example, the tubing 14 may have an inner diameter of 2.6 millimeters and an outer diameter of 4.0 millimeters, although the particular inner and outer diameters of the tubing are not critical.

The tubing 14 is of sufficient length to connect the probe 12 with the flow generator 16 and other components, which may vary from application to application. (A length of approximately 1.5 meters may be appropriate for most in-laboratory measurements, although longer or shorter lengths may be used in other settings and for other applications.) A connector 26 is provided at one end of the tubing 14 to connect the tubing 14 to the other components of the apparatus 10. One exemplary type of connector is shown in FIG. 2, although the actual connector 26 that is used will vary depending on the characteristics of the component(s) to which it is attached. The connector 26 should provide an airtight seal between the tubing 14 and the other components of the apparatus 10. As shown in FIG. 2, an in-line connector 28 may be used to connect shorter segments of tubing 14 together, or to connect the segment of tubing 14 on which the probe 12 is mounted with the rest of the tubing 14.

Figure 4:
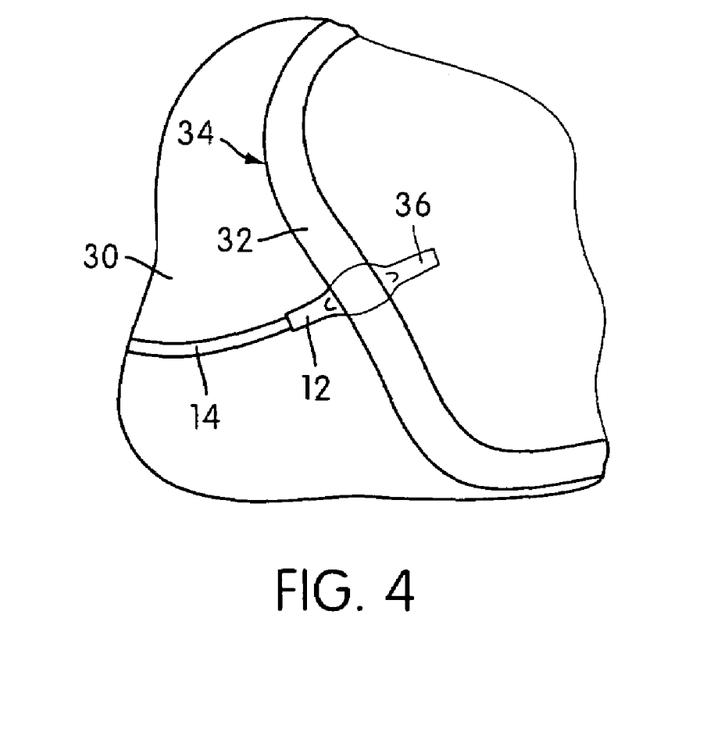
FIG. 4 is a top plan view of the pressure measurement probe operatively positioned between a breathable gas mask and a patient's skin.

The probe 12 is designed to be positioned between two contacting surfaces, as in the top plan view of FIG. 4, in which it is illustrated as positioned between skin 30 and the cushion 32 of a breathable gas mask 34. (Although a cushion 32 is shown in FIG. 4, breathable gas masks may alternatively use a conforming flange of soft rubber, such as silicone rubber and/or foam. Masks made with an inflatable chamber are also contemplated. The term "cushion," as used herein, is meant to encompass all of these structures and materials.) The probe 12 is usually positioned such that the end portion 36 of the probe 12 extends beyond the inner edge of the cushion 32. For example, the end portion 36 may extend about 10 mm beyond the inner edge of the cushion 32, towards the interior of the mask 34. The length of the end portion 34 of the probe 12 that extends beyond the interface between the two objects would depend on the width of the two objects and may be arbitrarily selected.

Figure 5A:
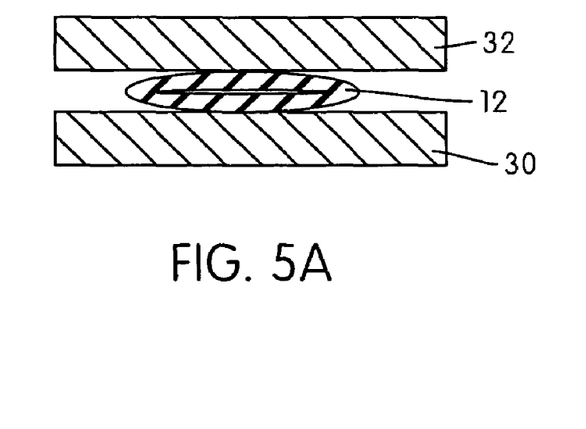
FIG. 5A is a sectional view of the compressed, operatively positioned pressure measurement probe.

The initial contact pressure between the skin 30 and the cushion of the breathable gas mask 34 causes the probe 12 to be compressed between the skin 30 and the mask 34, as shown in FIG. 4. The initial, compressed operative position of the probe 12 between the skin and mask 34 is also shown in FIG. 5A, a sectional view of the probe 12, skin 30, and mask cushion 32. Typically, the compressive forces on the probe 12 cause its open end to be entirely or almost entirely closed in the initial operative position. As pressure and flow are generated by the flow generator 16, the pressure within the probe 12 and tubing 14 grows until the internal pressure within the probe 12 and tubing 14 begins to overcome the contact pressure between the mask 34 and skin 30. When the internal pressure of the probe 12 begins to overcome the contact pressure between the mask 34 and skin 30, the end of the probe 12 is forced open, as illustrated in the sectional view of FIG. 5B, allowing flow though the open end of the probe 12. Data on the contact pressure between the mask 34 and skin 30 can be obtained by monitoring the pressure in the probe 12 and the flow through the probe 12. This process will be described in greater detail below.

Figure 5B:
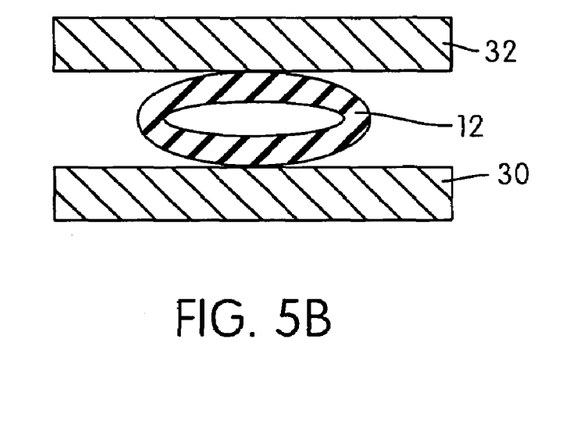
FIG. 5B is a sectional view similar to that of FIG. 5A showing the pressure measurement probe in a partially compressed operative position.
Figure 5C:
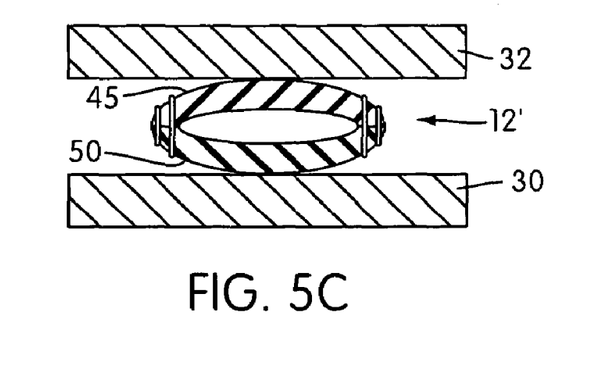
FIG. 5C illustrates a cross section of another embodiment of the present invention.

FIG. 5C shows an alternate embodiment of the present invention. In this embodiment, the probe 12' includes upper and lower side walls 45, 50 that are joined at each end, e.g., via glue, stitching, and/or the like.

As will be obvious from the previous paragraph, the probe 12 is adapted to withstand a defined internal pressure which is at least equal to the maximum contact pressure expected between the two objects, e.g., the skin 30 and mask cushion 32. For mask contact pressure applications, the probe 12 may be designed to withstand interior pressures up to about 40 cm $H_2O$. Other applications may require the probe 12 to operate at higher internal pressures. In higher-pressure applications, the walls of the probe 12 may have a greater thickness, or may be made of other materials, such as rubber materials with greater stiffness, metal foils, or deformable composite-reinforced materials. In general, the tubing 14 may be rated to handle the same pressure as the probe 12, or it may be rated to handle higher pressures.

The material from which the probe 12 is made should be strong enough in tension to contain whatever fluid pressures are required. However, it is desirable if the material is also relatively soft and compliant in bending/crushing, such that the force necessary to deform the probe 12 itself may be considered negligible. If the force required to deform the probe is negligible in comparison with the applied pressures, it may be ignored when taking pressure data with the apparatus 10. In embodiments of the invention, if the force required to deform the probe 12 is not negligible, the data acquisition system 22 or computing unit 24 may be configured or adapted to actively compensate for the force required to deform the probe 12. Compensation could be performed by, e.g., modeling the force-deformation response of a particular probe material and normalizing the acquired pressure data using the model for that particular probe material. Compensation could also be performed by using known, measured force-deflection data for a particular probe material to normalize the acquired pressure data.

Fluid flow and pressure within the pressure measurement system 10 are generated by the flow generator 16. The flow generator 16 may be a variable or constant pressure compressor adapted to compress room air, oxygen, or another mix of gases to desired pressures. (If mask contact pressure measurements are to be taken on a live subject, the mixture of gases may be either breathable or, if the patient is supplied with sufficient breathable gas, physiologically inert.) Preferably, the flow generator 16 should be able to provide a plurality of pressure values so that measurements can be made at each pressure value. For example, the flow generator 16 can be set to ramp up through a range of pressure values. "Desired pressures" for breathable gas mask contact pressure applications typically range from about 0 cm $H_2O$ to about 40 cm $H_2O$, although other pressures may be used for other applications. In breathable gas mask contact pressure applications, a variable positive airway pressure (VPAP) compressor such as the VPAP II STA (ResMed Ltd., North Ryde, NSW, Australia) may be used.

Alternatively, depending on the nature of the components, the gas or mix of gases may comprise noble gases, such as argon or helium. If the gas or gases are initially provided in high-pressure compressed gas cylinders, the flow generator 16 may be a gas pressure regulator configured to provide a gas flow at a desired pressure (which is typically lower than the gas storage pressure in the gas cylinder). A pressure regulator may also be used if the compressor used as the flow generator 16 is a constant pressure compressor.

Additionally, liquid fluids such as water may be used to generate the desired pressures and flow rates, depending on the nature of the pressure measurement application.

The internal pressure in the tubing 14 and probe 12, and the flow through the tubing 14 and out the open end of the probe 12, are measured by the manometer 18 and flow meter 20, respectively. The manometer 18 and flow meter 20 may be digital or analog instruments that are connected to the tubing 14 in series with the pressure generator 16 by appropriate connectors 26, 28. Examples of suitable digital instruments include electronic manometer model number PS 309 available from Validyne Engineering Company (Northridge, Calif., USA) and electronic flowmeter model number TSI 4040 available from TSI, Inc. (Shoreview, Minn., USA).

In the embodiment illustrated in FIG. 1, the manometer 18 and flow meter 20 are connected via data connections to the data acquisition system 22, although those of ordinary skill in the art will realize that the data acquisition system 22 and computing unit 24 are not required in order to obtain data from the pressure measurement system 10. Instead, especially if the pressure and flow rates in the tubing 14 and probe 12 rise slowly, data may be read directly from the manometer 18 and flow meter 20, e.g., manually.

The term "data acquisition system" is meant to encompass data acquisition hardware such as signal amplifiers, filters, and other signal conditioning equipment, as well as the breakout boxes and other components that make the physical data connection between the data acquisition system 22 and the manometer 18 and flow meter 20. Depending on the particular installation and available equipment, the data acquisition system 22 may be a stand alone unit, or its functions may be integrated into the computing unit 24. If the data acquisition system 22 is a stand alone unit, it may include sufficient computing and storage ability to acquire and store data points for later analysis and, thus, may not be connected to a separate computing unit 24 during data acquisition. Alternatively, the data acquisition system 22 could provide the computing unit 24 with data in real time.

One type of appropriate data acquisition system 22 is the DAQBOOK® 260 data acquisition system (IoTech, Inc., Cleveland, Ohio, USA), in which case the computing unit 24 may be a personal computer equipped with the DAQ-VIEW™ software (IoTech, Inc.). Other common data acquisition products and supporting software may be used, including LabVIEW®-based data acquisition systems (National Instruments, Inc., Austin, Tex., USA). Customized data acquisition software may also be created in a conventional programming language, such as C++ or Java. Depending on user needs, the computing unit 24 may also be equipped with more generalized analysis software, such as spreadsheet software. The data acquisition software of the computing unit 24 may also be adapted to provide the acquired pressure and flow data to mechanical modeling software, such as finite element method software or CAD software.

Those of ordinary skill in the art will realize that the computing unit 24 need not be a personal computer, or even a multipurpose computer. The computing unit 24 may be any type of computing device having numerical analysis capabilities commensurate with user needs. Other types of computing units include microprocessors or ASICs coupled with appropriate memory and display devices. Depending on the capabilities of the computing unit 24, the analysis software may be hard-coded into the computing unit 24 in a lower-level programming language, such as assembly code.

Figure 6:
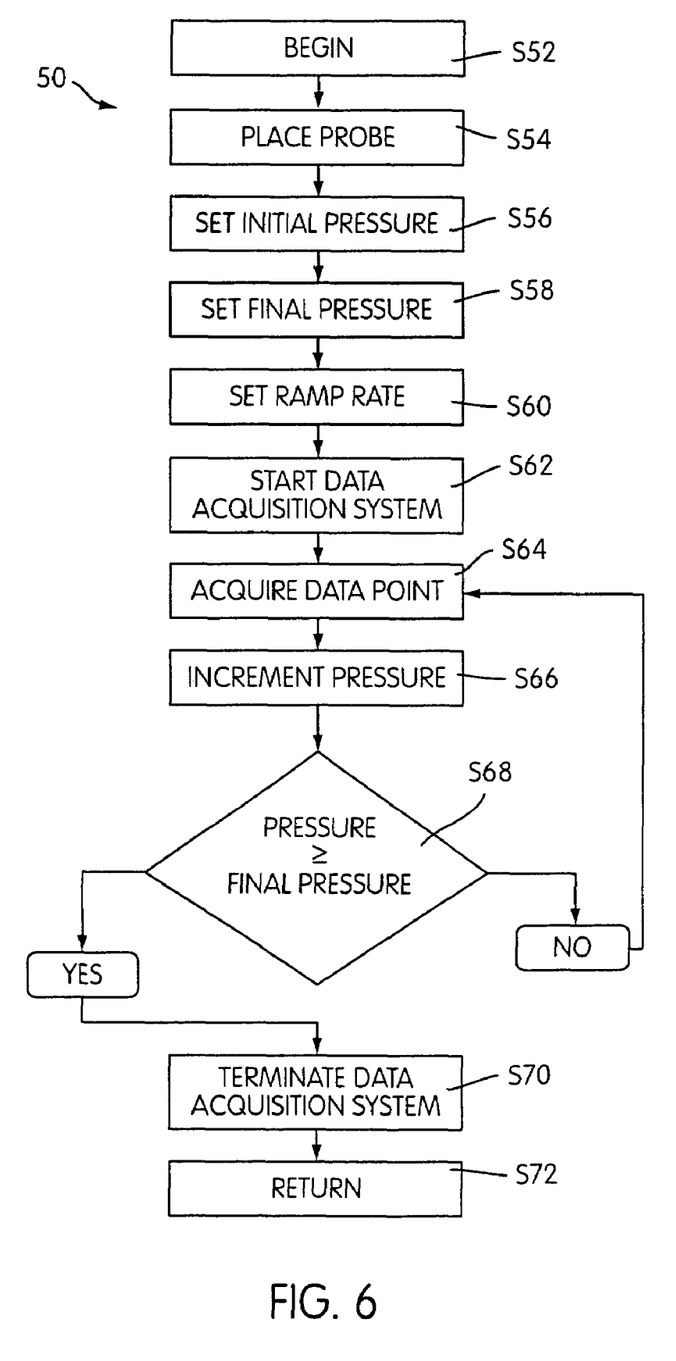
FIG. 6 is a high-level schematic flow diagram of a method of using the pressure measurement system of FIG. 1.

A method 50 of using the pressure measurement system 10 is shown in the high-level schematic flow diagram of FIG. 6. Method 50 begins at S52 and continues with S54. At S54, the user places the probe 12 between the two contacting objects, for example, between the mask 34 and the skin 30, as in FIG. 4. The probe 12 is inserted between the mask 34 and skin 30 such that it does not wrinkle or distort, which might create unwanted flow obstructions. Once the probe 12 is placed in S54, the user may begin the typical regimen usually used with the mask 34, for example, variable positive airway pressure. (Treatment regimens would typically be implemented using a separate flow generator, not the flow generator 16 used in the pressure measurement system 10.) Method 50 continues with S56, at which the user sets the initial pressure of the flow generator 16, and S58, at which the user sets the final pressure of the flow generator 16. Depending on the type of flow generator 16 and the data acquisition system 22, the user may simply activate the data acquisition system 22 at this point and allow it to acquire data from the manometer 18 and flow meter 20 while the flow generator 22 ramps from the initial to the final pressure. The remaining tasks illustrated in method 50, and the following description, assume that the flow generator 16 is controlled by the data acquisition system 22.

Method 50 then continues with S60, at which the user sets the ramp rate of the flow generator 16. Once the ramp rate is set in S60, the flow generator 16 is activated and the user begins data acquisition (DAQ) at S62. At S64, the data acquisition system 22 acquires a data point and control passes to S66, at which the data acquisition system 22 increments the flow generator 16 pressure. Alternatively, the pressure can be incremented manually. Control then passes to S68. At S68, the data acquisition system 22 or computing unit 24 compares the current flow generator 16 pressure with the desired final pressure. If the current pressure is greater than or equal to the desired final pressure (S68:YES), control passes to S70 and the data acquisition terminates. Otherwise (S68:NO), control returns to S64 and another data point is acquired. Method 50 terminates and returns at S72.

Figure 7:
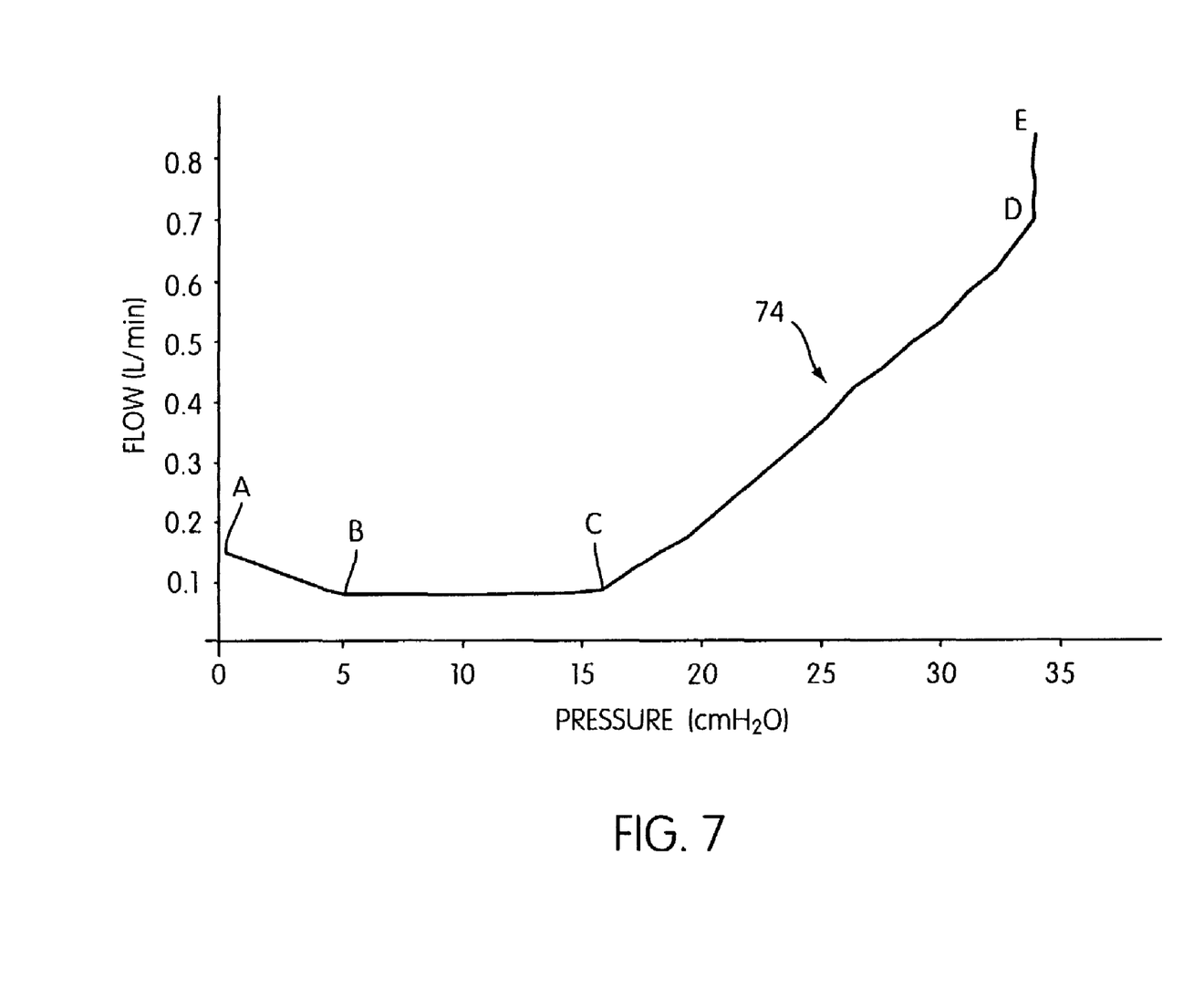
FIG. 7 is a schematic waveform illustrating pressure and flow data that may be generated by the pressure measurement system of FIG. 1.

FIG. 7 illustrates a schematic waveform 74 of pressure versus flow data that may be generated by the pressure measurement system 10 using a method such as method 50. In FIG. 7, exemplary units and numerical values are shown for a mask/skin contact pressure measurement application, although those of ordinary skill will realize that the pressures and flow rates will be different in different applications, and that the results may be reported in any convenient units. Initially, the probe 12 is seated between the mask 34 and skin 30, as in FIG. 4, and is compressed and substantially sealed by the contact pressure between the two. During segment A-B of waveform 74, pressurized gas fills the initially unpressurized tubing 14 and probe 12. During segment B-C, the pressure in the probe 12 continues to increase, but does not overcome the contact pressure between the mask 34 and skin 30, and so the probe 12 stays closed, allowing only a constant, insubstantial amount of gas to flow out. During segment C-D, the pressure in the probe 12 exceeds the contact pressure between the mask 34 and skin 30, causing the probe 12 to begin opening and, consequently, causing the amount of flow through the tubing 14 and probe 12 to increase. (The pressure at point C, approximately 16 cm $H_2O$, would be taken as the contact pressure between the mask 34 and skin 30.) In segment D-E, pressure in the probe 12 has caused the mask 34 to lift completely away from the skin 30. In the illustrated mask/skin application, method 50 may be executed such that the pressure in the probe 12 ramps from 0 cm $H_2O$ to 36 cm $H_2O$ in about 15 seconds.

Method 50 and waveform 74 illustrate the acquisition of a single contact pressure data point. However, the pressure measurement system 10 may also be used to gather multiple contact pressure data points in the same location over time. For example, instead of increasing pressure substantially beyond the contact pressure (i.e., as in segment D-E of waveform 74) and terminating data acquisition, the pressure within the tubing 14 and probe 12 could be reduced quickly to a pressure that is lower than the contact pressure between the two surfaces. Once pressure within the tubing 14 and probe 12 is reduced, it could then be increased again while continuing data acquisition, which would generate another contact pressure data point. This process could be repeated at intervals, for example, to generate a contact pressure data point every few seconds. Data points may be taken at essentially any desired data acquisition rate, subject only to the frequency limitations of the data acquisition hardware (including the data acquisition system 22 and flow meter 20). (Those of skill in the art will appreciate that at higher frequencies, some materials, such as skin, respond nonlinearly to the application of pressure, an effect which may or may not be desirable, depending on the application.) Typically, it is preferable to gather at least two data points at each particular pressure, and may be more preferable to gather about ten data points per particular pressure.

The embodiment described above involves the use of a single probe 12 to collect contact pressure at one location between two surfaces. However, in other embodiments, multiple probes 12 may collect contact pressure data at a plurality of locations simultaneously.

Figure 8:
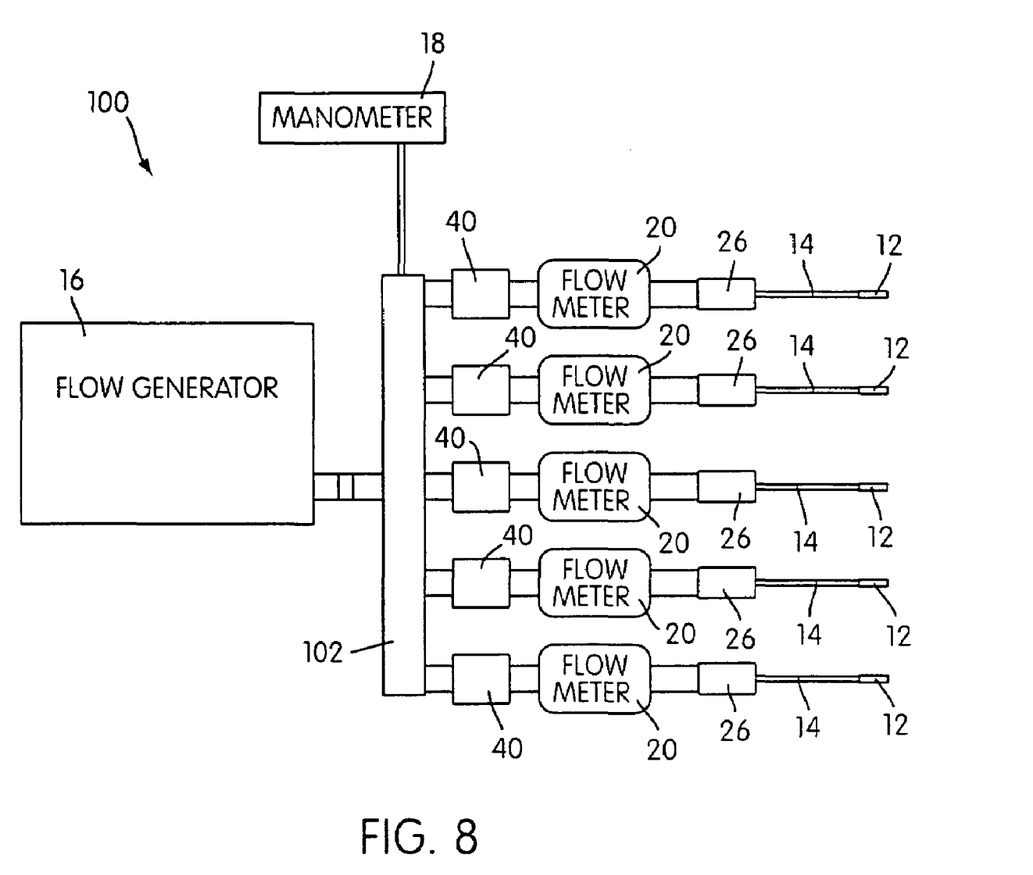
FIG. 8 is a schematic illustration of a pressure measurement system according to another embodiment of the present invention in which multiple pressure measurement probes are used simultaneously.

A multiple-probe embodiment of a pressure measurement system 100 according to the present invention is illustrated schematically in FIG. 8. The data acquisition system 22 and computing unit 24 are not shown in FIG. 8, although they would be connected to the pressure measurement system 100 in the same way as illustrated in FIG. 1. In general, only those portions of the pressure measurement system 100 that differ from those in pressure measurement system 10 are described; the description above will suffice for the other components.

In pressure measurement system 100, the flow generator 16 is connected to a connection block 102. The connection block 102 has a plurality of outlets (five in FIG. 8) to which individual lengths of tubing 14 can be connected, such that flow from the flow generator 16 is divided and flows through the tubing 14 and into a corresponding plurality of probes 12. The individual probes 12 are connected in parallel with respect to each other. A flow meter 20 is connected in series with each one of the plurality of probes 12, and a single manometer 18 is connected to the connection block 102. A plurality of valves or switches 40 can be selectively activated to control flow through each of the outlets. Alternatively, a single flowmeter 20 could be provided, if that flowmeter was capable of taking individual flow measurements for each of the probes 12. In yet another alternative, a plurality of manometers may be provided, one for each outlet.

Figure 9:
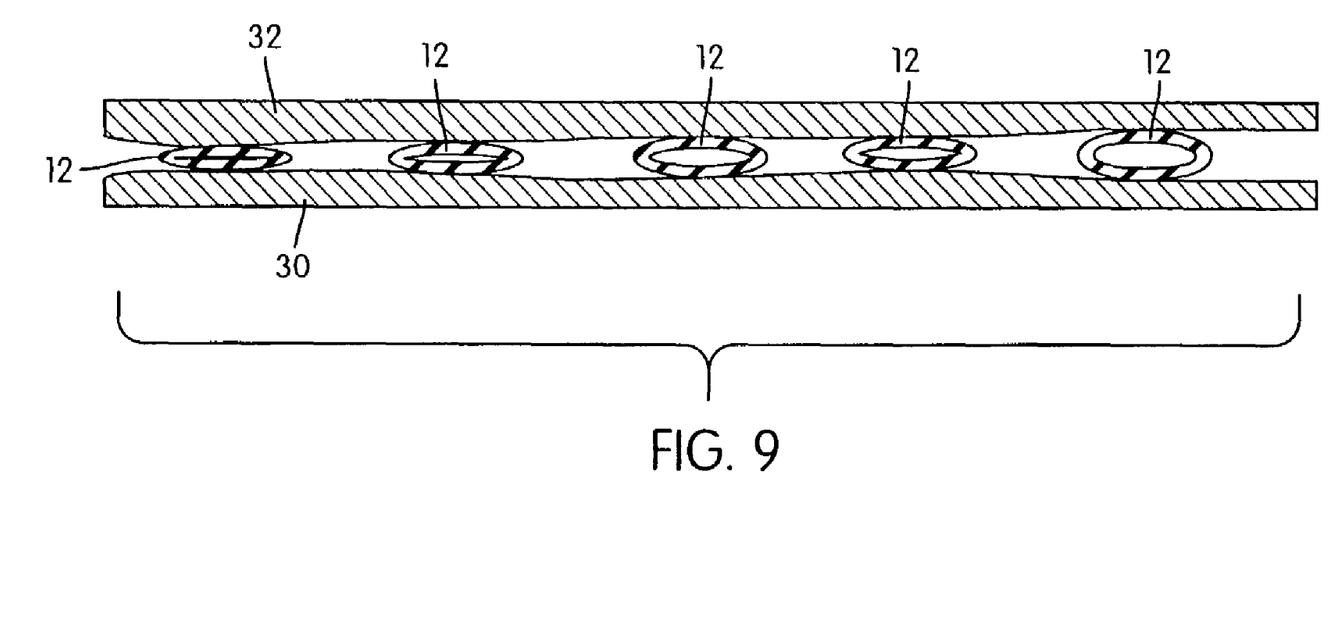
FIG. 9 is a sectional view similar to those of FIGS. 5A and 5B, illustrating the multiple pressure measurement probes of the pressure measurement system of FIG. 7 installed in operative positions along an interface.

Multi-probe pressure measurement system 100 allows a user to simultaneously gather contact pressure data at several points along an interface between two surfaces. For example, FIG. 9 is a sectional view similar to that of FIGS. 5A and 5B, illustrating several probes 12 operatively positioned between skin 30 and the cushion 32 of a mask 34. As shown, the contact pressures between the mask cushion 32 and the skin 30 are different at each point, thus the individual probes 12 are each compressed to varying degrees, and consequently, the flow through each probe 12 is different (ranging from essentially no flow for the probe 12 on the extreme left of FIG. 9 to considerable flow for the probe 12 on the extreme right of FIG. 9). Although the probes 12 are shown as linearly adjacent in FIG. 9 for clarity of illustration, they need not be linearly adjacent in actual use. Instead, they may be arranged in any way. Additionally, if only a few of the available probes 12 are to be used for a particular measurement task, the connection block 102 could be provided with an individual shut-off valve for each probe, such that flow from the flow generator 16 would not flow into the unused probe 12. Alternatively, the user may disconnect the unused probes 12 from the connection block 102 and install appropriate caps to seal the open outlets of the connection block 102.

Once contact pressures have been determined over an area of the interface between two surfaces, a map can be created, illustrating how the contact pressures vary along the interface. A contact pressure map such as this may be used to design or custom fit a breathable gas mask or other device for a better fit. For example, an existing breathable gas mask may be modified in accordance with contact pressures determined by using a method such as method 50. This may be done iteratively. For example, a user could perform method 50 on an existing mask to create a contact pressure maps of that mask on a representative group of subjects or models. Using the pressure maps, the user would then "build up" the mask where contact pressures are consistently low and "cut down" the mask where contact pressures are consistently high to obtain the desired distribution, e.g., a more even pressure distribution. In another embodiment, the desired pressure/force distribution may be uneven, to apply less pressure/force on sensitive areas and more pressure/force or less sensitive areas, preferably while providing the user with an improved comfort level and/or the appearance of an even pressure distribution. The new or improved mask design could then be validated by performing method 50 again.

Additionally, contact pressure maps may be used to create accurate models, both computational and physical, of human faces and other body parts. These model faces and other body parts may be created using contact pressure maps from several experimental subjects, and may be made in a range of "standard" sizes. The "standard" sizes for these models may, for example, represent mean anthropometric values for desired body parts or facial features, plus or minus a number of standard deviations. The model faces and other body parts would then used to design and test breathable gas masks and other devices.

Certain components of the apparatus 10 may be built into a breathable gas mask or other component to be tested, such that a testing method like method 50 may be employed without providing a separate probe 12.

Although the invention has been described with respect to several exemplary embodiments, those of ordinary skill will realize that variations and modifications are possible within the scope of the invention. The embodiments described herein are intended to be exemplary only and are not to be construed as limiting.

What is claimed is:

1. A method for measuring contact pressure between a cushion and a surface of a patient's face, comprising:

providing at least one deformable probe having a flow passage therein, said flow passage being adapted for communication with and/or connection to a source of pressurized air;

inserting the probe between the cushion and the surface of the patient's face;

urging the cushion against the surface of the patient's face such that the probe is deformable from a normally open flow passage configuration to a substantially closed flow passage configuration; and measuring fluid pressure within the probe and fluid flow through the probe to provide a measure of the contact pressure.

2. The method of claim 1, further comprising measuring an amount of opening of the flow passage as a measure of the contact pressure.

3. The method of claim 1, further comprising creating a contact pressure map from contact pressures over an area of interface between the cushion and the surface of the patient's face, and using the contact pressure map to develop a customized mask.

\* \* \* \* \*